(12) United States Patent
Hort et al.

(10) Patent No.: US 9,891,201 B2
(45) Date of Patent: Feb. 13, 2018

(54) METHODS

(71) Applicant: Mars, Incorporated, Mclean, VA (US)

(72) Inventors: Joanne Hort, Nottinghamshire (GB); Andrew Taylor, Leicestershire (GB); Neil Desforges, Leicestershire (GB)

(73) Assignee: Mars, Incorporated, McLean, VA (US)

(*) Notice: Subject to any disclaimer, the term of this patent is extended or adjusted under 35 U.S.C. 154(b) by 93 days.

(21) Appl. No.: 14/427,248

(22) PCT Filed: Sep. 10, 2013

(86) PCT No.: PCT/EP2013/068751
§ 371 (c)(1),
(2) Date: Mar. 10, 2015

(87) PCT Pub. No.: WO2014/037587
PCT Pub. Date: Mar. 13, 2014

(65) Prior Publication Data
US 2015/0346176 A1 Dec. 3, 2015

(30) Foreign Application Priority Data

Sep. 10, 2012 (GB) .................................. 1216074.3
Apr. 22, 2013 (GB) .................................. 1307204.6

(51) Int. Cl.
*G01N 33/02* (2006.01)
*G01N 33/00* (2006.01)

(52) U.S. Cl.
CPC ......... *G01N 33/02* (2013.01); *G01N 33/0001* (2013.01)

(58) Field of Classification Search
CPC ........................... G01N 33/02; G01N 33/0001
(Continued)

(56) References Cited

U.S. PATENT DOCUMENTS 3,686,930 A * 8/1972 Kniebes ............. G01N 33/0001
436/119
3,882,713 A * 5/1975 Nishida ............. G01N 33/0001
73/23.34
(Continued)

FOREIGN PATENT DOCUMENTS

| EP | 1216622 A2 | 6/2002 |
|---|---|---|
| JP | 4974383 B2 * | 7/2012 |
| WO | 2005-078433 A1 | 8/2005 |

OTHER PUBLICATIONS

Schieberle et al. Evaluation of the Character Impact Odorants in Fresh Strawberry Juice by Quantitative Measurments and Sensory Studies on Model Mixtures, J. Agric. Food Chem., 45:227-232, 1997.*

(Continued)

*Primary Examiner* — Hezron E Williams
*Assistant Examiner* — Marrit Eyassu
(74) *Attorney, Agent, or Firm* — Mars, Incorporated

(57) ABSTRACT

The present invention relates to a method of analyzing the components of a flavor sample comprising the steps of a) preparing a composition comprising a number (n) of aroma compounds to form a replica of a flavor; b) preparing a further composition comprising the same aroma and/or taste compounds with one of the components being reduced in amount by from 5 to 95% compared to the amount in the first composition; and c) comparing the aroma and/or taste of the first and second compositions.

19 Claims, 2 Drawing Sheets

Figure 1:
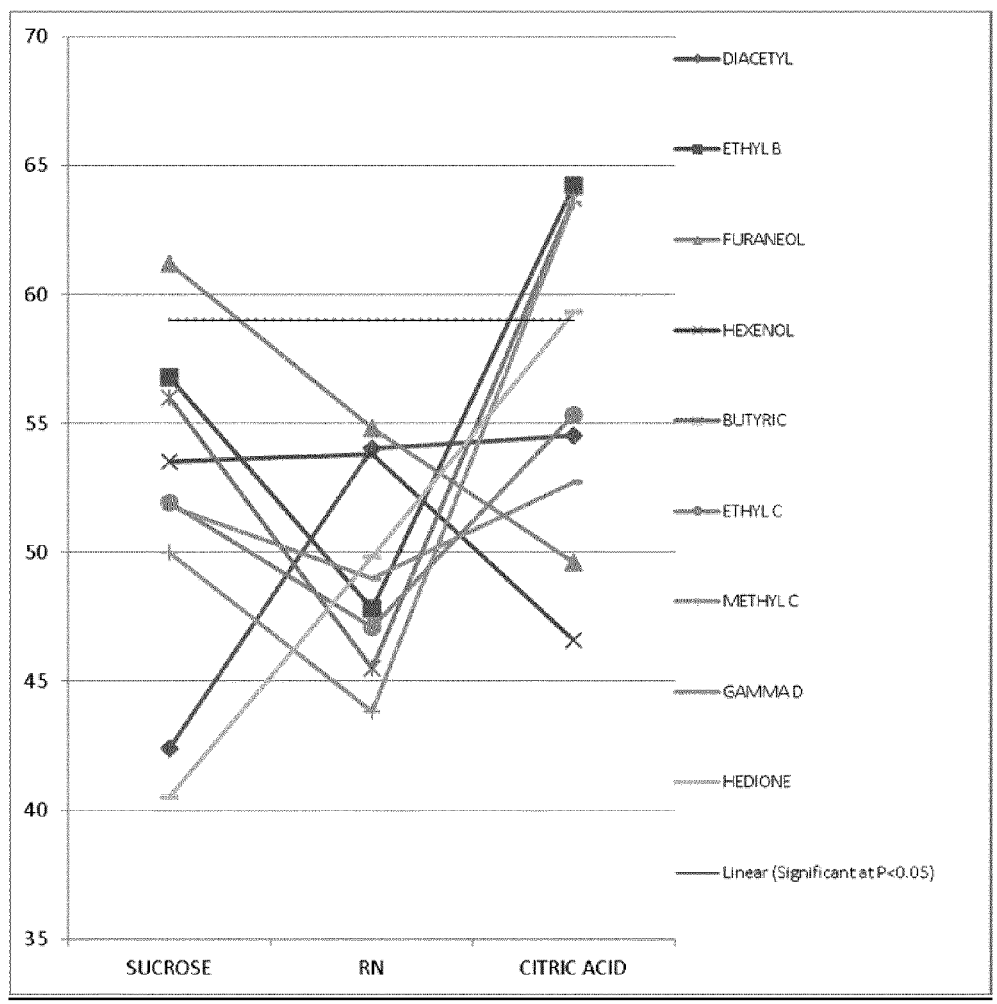

(58) Field of Classification Search
USPC .......................................... 73/23.34, 865.7
See application file for complete search history.

(56) References Cited

U.S. PATENT DOCUMENTS

| | | | | |
|---|---|---|---|---|
| 5,355,718 | A * | 10/1994 | Mookherjee | G01N 33/02 47/69 |
| 7,167,815 | B2 * | 1/2007 | Labreche | G01N 33/0034 702/193 |
| 7,288,515 | B1 * | 10/2007 | Winkler | A61L 9/01 512/1 |
| 2002/0076473 | A1 * | 6/2002 | Reinders | A23C 9/1307 426/534 |
| 2003/0072733 | A1 * | 4/2003 | McGee | A01K 1/0152 424/76.4 |
| 2006/0093720 | A1 * | 5/2006 | Tatz | A23L 29/20 426/548 |
| 2007/0191257 | A1 * | 8/2007 | Andretta | A61Q 13/00 512/1 |
| 2009/0234196 | A1 * | 9/2009 | Suzuki | G01N 33/14 600/300 |
| 2009/0305423 | A1 * | 12/2009 | Subramanian | G01N 33/04 436/22 |
| 2011/0318459 | A1 * | 12/2011 | George | A23L 27/20 426/302 |
| 2012/0237660 | A1 * | 9/2012 | Flamme | A21D 2/14 426/548 |

OTHER PUBLICATIONS

Zamora, Maria Clara et al, "Sourness? Sweetness Interactions in Different Media: White Wine, Ethanol and Water." Journal of Sensory Studies, vol. 21, No. 6, Dec. 1, 2006, pp. 601-611.

Malundo, T.M.M et al, "Flavor quality of fresh tomato (Lycopersicon esculentum Mill.) as effected by sugar and acid levels." Postharvest Biology and Technology, vol. 6, No. 1-2, Jun. 1, 1995.

Grosch, W, "Evaluation is the Key Odorants for Foods by Dilution Experiments, Aroma Models and Omission," Chemical Senses, vol. 26, No. 5, Jun. 1, 2001.

Park et al, A Comparison of the Discriminating Power of Anova and R-Index Analyses of Hedonic Data for Various Products and Experimental Protocols, Journal of Sensory Studies, 22, 281-292, 2007.

Schieberle, et al., "Evaluation of the Character Impact Odorants in Fresh Strawberry Juice by Quantitative Measurements and Sensory Studies on Model Mixtures", J. Agric. Food Chem., 45: 227-232, 1997.

* cited by examiner

METHODS

The present invention relates to a method of analysing the components of a flavour sample comprising the steps of a) preparing a composition comprising a number (n) of aroma compounds to form a replica of a flavour; b) preparing a further composition comprising the same aroma and/or taste compounds with one of the components being reduced in amount by from 5 to 95% compared to the amount in the first composition; and c) comparing the aroma and/or taste of the first and second compositions.

Current practices in aroma and flavour evaluation tend toward the use of instrumental analysis. This can dictate which compounds, and their relative quantities, are used to manufacture a synthetic replicate for use in the food and fragrance industry. However, it is now becoming more important for these industries to understand not only how to formulate an aroma mixture but in fact how these aroma mixtures are perceived by the consumer. Through the use of sensory evaluation of known aroma mixtures, valuable information can be obtained on the characteristics of each compound and its purpose within the mixture. So far, there has been some effort to establish a basis for omission studies using various sensory methodologies, but prior to the present invention, a rigorous sensory method had yet to be developed.

The literature on recombination methodology is spread across different publication types. Journal papers contain little experimental detail and rationale about the sensory methods generally refer back to a single paper; Grosch (2001, Chem. Senses 533-545). This paper describes omission experiments, wherein a synthetic blend of odorants (compounds) is used as a model for a particular aroma. The compounds essential for replicating the aroma are identified by omitting each compound individually (n−1; n being the number of aroma compounds in the blend), until the assessor can no longer identify the aroma that is being replicated, or the assessor indicates that the aroma has changed from the full composition.

Generally, the method employed to replicate food aromas is to recombine the individual odours that have been identified (often using the amounts measured in the original product) to make a recombination test mixture. This recombined odour is then assessed sensorially against the original sample and the sensory panel "match" will indicate whether the key odorants have been captured in the chemical analyses or whether addition of some other components can improve the "match". This step ensures that the instrumental and sensory analyses in the identification and quantification steps of the analytical procedure have captured the key odorants.

Since it is well-established that there are physical/cognitive interactions between odorants which affect sensory perception, the recombination step also allows these interactions to be studied using an omission approach. One component is left out of the mixture in turn and the sensory quality measured. From this approach, the interaction of components can be elucidated.

However, the methods described by Grosch and presently widely used are very much binary; an aroma compound is considered either necessary or unnecessary. Only qualitative data are generated, when it may be more useful to determine quantitative data with regard to the individual components. Furthermore, the aroma compounds are tested by sense of smell alone, which does not take into account the part played by the sense of taste in flavour perception, identification and/or replication.

Therefore, there is a need to develop a robust sensory protocol for use in assessing overall and individual quality attributes of aroma compounds for omission experiments.

Accordingly, the present invention provides a method of analysing the components of a flavour sample comprising the steps of:

a) preparing a composition comprising a number (n) of aroma and/or taste compounds to form a replica of the flavour;
b) preparing a further composition comprising the same aroma and/or taste compounds with one of the components being reduced in amount by from 5 to 95% compared to the amount in the first composition; and
c) comparing the aroma and/or taste of the first and second compositions.

The comparison of step c) is carried out by smell or by taste.

The omission of just part of the total amount of a compound, rather than omitting it in its entirety means that the invention allows for additional and useful information to be gathered, which is important in the development of flavours.

The method allows for a more accurate assessment of whether a particular compound is essential to the flavour being assessed, and whether it is required in a minimum (or maximum) amount in order to be perceived. Therefore, the invention provides that the component that is reduced in the second or further composition is reduced by from 5 to 95%, rather than being omitted completely as previously known in the art. The compound to be reduced may be reduced by from 10 to 90%, from 20 to 80%, from 30 to 70, from 40 to 60% or by about 50%. The compound to be reduced may be reduced by about 25%.

The method of the invention may also comprise comparing more than one altered composition to the original composition. For example, the method may comprise producing a further composition comprising the same aroma and/or taste compounds as the first composition, with a different one of the components than that changed in the second composition being reduced in amount by from 5 to 95% compared to the amount in the first composition; and wherein step c) comprises comparing the first, second and further compositions.

Alternatively, a first composition may be produced that has the same compound altered as in the second composition, but in a different amount, such that the 100% level and two different levels of altered/reduced levels of that compound may be directly compared.

It may also be envisaged that the invention includes a method that involves the reduction of more than one compound in the second or further compositions, alongside or after analysis of the individual component reduction.

To develop the invention, a nine component strawberry flavour was used. This flavour profile is well known, the aroma components well established and recognised by one skilled in the art. The method of the invention has also been carried out with a savoury flavour. By savoury, it is meant, salty, meaty or spicy and not sweet.

In the present invention, suitable checks for the recombination step especially with regard to statistical power in the human sensory panel and appropriate presentation of the odour samples were developed. The recombination step was improved by considering alternative types of omission test and the development of a "taste base" to monitor taste-odour interactions and improve the ability to identify key flavour combinations.

The present invention was developed using a nine component strawberry flavour to determine how the overall and individual sensory attributes vary when the formulation is changed using the standard and revised omission approaches. The strawberry flavour formulation provides a sufficiently simple system that is palatable and where the overall aroma and flavour is clearly recognised as strawberry. The concept of using a reduced level of one component rather than completely removing the component is a more sophisticated approach to recombination and will maximise the chances of measuring taste and odour interactions within the mixture. The actual level of reduction may be established by varying the level of omission depending on the odour strength of the individual component.

The composition to be tested may contain 2 or more components. Preferably, it may contain 5 to 20 components, or 6, 7, 8, 9, 10, 11, 12, 13, 14, 15, 16, 17, 18, 19, or 25, 30 components.

With sensory testing there is always a concern that the assessors do not reflect the general population due to the low numbers or the use of expert assessors. Using a Same-Different test (ASTM-E2139-05) with a larger panel of untrained assessors overcame this concern. Use of the R-index method with an 8 point surety rating allows a robust statistical procedure to be applied in data analysis. When assessors make a decision if the samples are same or different, they apply a "very sure", "sure", "unsure" or "very unsure" rating to their same/different response. This additional information removes the psychological response bias that may occur otherwise.

The use of the Same-Different sensory method proved to be a very effective tool in assessing the impact of different compounds within an aroma mixture. The surety rating is an indispensable way to ensure the resulting data is robust and as such, superseded the Chi squared statistical method in the development of this protocol. The technique is easily applied at both experimental design, testing and data analysis stages of omission experiments, contributing to its expansive uses for industry whether this involves sniffing type assessments (orthonasal testing), or drinking and eating assessments (retronasal testing).

In order to investigate further the impact of taste as well as smell, the aroma compounds were formulated in a drinkable formulation with a water base, or with either a sweet or an acidic (sour) base. This was to determine whether the same compounds are perceived to be important when tasting the flavour rather than smelling it, and whether the addition of a component that is known to act on the tongue alters that perception, the so called multimodal perception or taste-aroma interaction Therefore, the present invention also includes a method of wherein the first and second formulation further comprise one of more taste compounds such as a sweet, sour, salt, bitter, heating, cooling, astringent, nutrient or umami compound. Examples of such compounds are as follows: sweet tasting compound, such as sucrose; an acidic component, such as citric acid; a bitter tasting component, such as quinine; a salty tasting component, such as sodium chloride; or a umami tasting component, such as monosodium glutamate. It will be appreciated by the skilled person that alternative representatives of these tastes may be used, as well as other tastes or sensations, such a hot (spicy, such as chili), cooling (such as menthol; peppermint) or astringent (such as tannin).

The use of additional base flavours in the compositions can help to ensure that any flavour developed will reflect the natural flavour, even when combined with for example, a food matrix e.g. a potato crisp or a pet food or a soft drink etc. Ensuring that the flavour remains true when mixed with a different base ingredient is clearly important, and the present inventors have found that using the method of the invention allows such flavour compositions to be altered accordingly.

Once the comparison has been carried out, statistical analysis may be performed in accordance with any suitable way known in the art. For example, ANOVA, Chi squared or R index as described in Park et al., (2007) Journal of Sensory Studies, 22, 281-292

Figure 2:
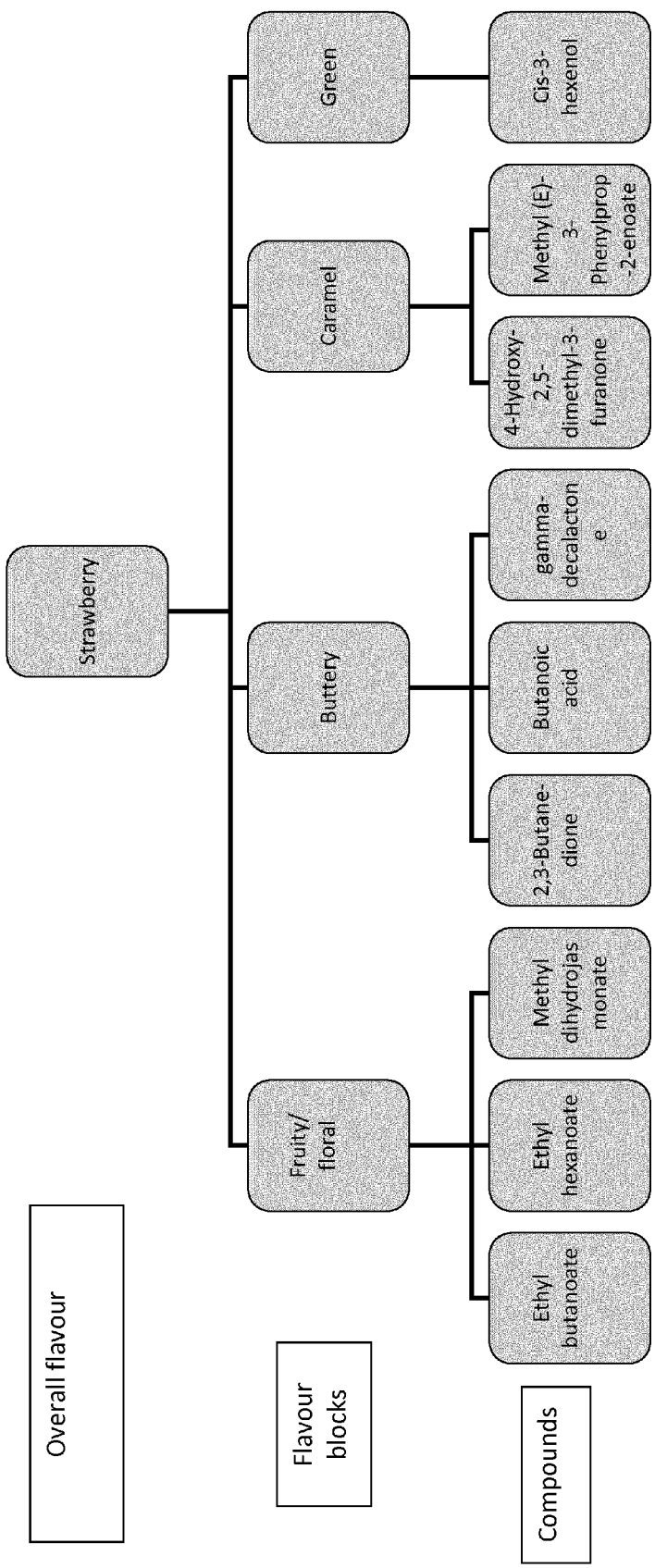

The invention will now be described with reference to the non-limiting examples and figures in which:

FIG. 1 shows Graphical representation of results from a n−0.5 test of the nine component strawberry mixture in the presence of a sucrose solution, water (RN) and a citric acid solution, and wherein the effect of the different taste compounds on the relative importance of the odour compounds can be clearly seen; and FIG. 2 shows the flavour blocks for the compounds of the synthetic strawberry flavour.

EXAMPLES

Example 1 n: A nine component synthetic strawberry aroma prepared in propylene glycol (Table 1) was dissolved in water at a suitable concentration to deliver a pleasant strawberry flavour.

n−1×1−9: 9 samples made omitting one different compound from each sample n−0.5×1−9: 9 n−0.5x samples made omitting 50% of an individual compound Samples were prepared to a specified liquid formulation and all aroma and taste samples were food grade and were obtained from commercial sources. The composition was as set out in the table below:

TABLE 1

| Composition of nine component strawberry flavour mixture | |
|---|---|
| COMPOUND | Composition g/kg |
| Methyl dihydrojasmonate | 0.003 |
| 2,3-Butanedione | 0.005 |
| 4-Hydroxy-2,5-dimethyl-3-furanone | 71 |
| Butanoic acid | 0.92 |
| cis-3-Hexen-1-ol | 10.5 |
| Methyl (E)-3-phenylprop-2-enoate | 2.5 |
| Ethyl butanoate | 5.2 |
| Gamma-decalactone | 1.35 |
| Ethyl hexanoate | 3.34 |
| Propylene glycol | 904 |

Method
Sniffing (Orthonasal) Testing 1 (n−1×1−9):
  Samples presented in bottles and sniffed by 100 naïve assessors under standard sensory testing conditions.
  Odour assessed with Same-Different test and an eight point surety rating (same/different: very sure, sure, unsure, very unsure).
  9 same/different tests in total, comparing the n−1×1−9 samples with the strawberry flavour 'n' with balanced presentation order (i.e., each of the samples was missing a different one of the components in its entirety).

Subjects asked to sniff both samples in the order presented and decide whether they smelled the same or different.

Sniffing (Orthonasal) Testing 2 (n−0.5×1−9):

Identical to Orthonasal testing 1 but using n−0.5×1−9 samples (i.e. each of the samples had the amount of a different aroma component reduced by 50%).

Data Analysis

Pearson's Chi Squared statistical test to test for significance.

R-index calculated from the surety rating, to test for significance after removing any response bias associated with the Same-Different test. Response bias is a cognitive factor which determines how cautious the assessor feels that a difference exists between samples. This is independent of the assessors' ability to tell a difference between the samples. The additional sureness judgement provides an alternative way of avoiding the effect of response bias by providing a way for this cognitive factor to be accounted for in the data analysis.

100 naive people were recruited to assess the compositions.

Results & Discussion

From Table 2 several comparisons can be made between:
1—the data analysis methods;
2—the two orthonasal tests; and
3—the data output for each compound.

1. The Chi-squared analysis highlights that the removal of seven compounds had a significant effect in the n−1×1−9 trial. Applying the R-index technique and removing response bias shows all nine compounds have a statistically significant effect on strawberry aroma. The increased validity from the R-index method renders the typical use of the Chi-squared statistical test in this Same-Different protocol as redundant.

2. The n−1×1−9 trial demonstrates the importance of all nine compounds when matching the strawberry aroma compared to the n−0.5×1−9 trial where just three compounds can be deemed as significant (R-index analysis), highlighting the varying sensitivity to different compounds and how this affects the overall perception of the strawberry flavour 3. The compounds with the most notable impact comparing the n−x and n−0.5x R-indices, are: Ethyl hexanoate—Almost no change in significance with the n−1 and n−0.5 tests so important to the strawberry flavour and no economical or quality merit to potentially reducing the amount of compound.

4-Hydroxy-2,5-dimethyl-3-furanone—traditionally considered as one of the most important compounds in a strawberry flavour but removing 50% does not illicit a significant difference which suggests this compound has a lesser effect on the overall flavour perception than other compounds like ethyl hexanoate.

TABLE 2

Results of n-1 and n-0.5 protocols with R-index and Chi squared statistical analyses

| | n-x | | n-0.5x | |
|---|---|---|---|---|
| COMPOUND | R INDEX (%) | CHI SQUARED | R INDEX (%) | CHI SQUARED |
| Methyl dihydrojasmonate | 68.9* | 10.5 | 46.7 | 0.4 |
| 2,3-Butanedione | 61.7* | 2.2 | 51.8 | 0.2 |
| 4-Hydroxy-2,5-dimethyl-3-furanone | 72.2* | 11.6* | 52.3 | 1.0 |
| Butanoic acid | 68.3* | 10.7* | 52.3 | 0.6 |
| cis-3-Hexen-1-ol | 76.4* | 12.1* | 52.8 | 0.6 |
| Methyl (E)-3-Phenylprop-2-enoate | 78.8* | 19.9* | 55.2 | 0.2 |
| Ethyl butanoate | 75.7* | 8.2* | 62.0* | 1.5 |
| Gamma-decalactone | 69.3* | 10.7* | 64.1* | 5.8* |
| Ethyl hexanoate | 68.7* | 0.1 | 68.5* | 8.0* |

Table 3 summarises the effect of changing the level of the individual components on overall strawberry flavour using the n−1 and n−0.5 protocols. With n−1, diacetyl has the lowest effect (R-index=61.7%) although this is still a significant effect. With the n−0.5 approach, a more detailed assessment can be made. Only three compounds have a significant effect showing that varying the proportion of these compounds in the test mixture has a major effect whereas methyl (E)-3-phenylprop-2-enoate has a medium effect, 55%, just above chance with the remaining compounds having no significant effect.

TABLE 3

Compounds affecting flavour differences using the n-1 and n-0.5 omission protocols

| Effect on flavour | n-1 | | n-0.5 | |
|---|---|---|---|---|
| Low | 2,3-Butanedione | 61.7* | Methyl dihydrojasmonate | 46.7 |
| | | | 2,3-Butanedione | 51.8 |
| | | | 4-Hydroxy-2,5-dimethyl-3-furanone | 52.3 |
| | | | Butanoic acid | 52.3 |
| | | | cis-3-Hexen-1-ol | 52.8 |
| Medium | Butanoic acid | 68.3* | Methyl (E)-3-Phenylprop-2-enoate | 55.2 |
| | Ethyl hexanoate | 68.7* | | |
| | Methyl dihydrojasmonate | 68.9* | | |
| | gamma-decalactone | 69.3* | | |
| High | 4-Hydroxy-2,5-dimethyl-3-furanone | 72.2* | Ethyl butanoate | 62.0* |
| | Ethyl butanoate | 75.7* | gamma-decalactone | 64.1* |
| | cis-3-Hexen-1-ol | 76.4* | Ethyl hexanoate | 68.5* |
| | Methyl (E)-3-Phenylprop-2-enoate | 78.8* | | |

Example 2

Drinking (Retronasal) Test

The experiments were repeated as above but the compositions were formulated for tasting, with water, a sweet base or a sour base and were assessed using the n−1 and the n−0.5 methodology. The sucrose was present at an amount of 2% w/v and the citric acid at 0.1% w/v. The concentration of the flavour mixture in each of the three compositions was 0.75%. Samples were placed in mouth, swallowed and the samples assessed to record whether they were the same or different.

n-1: Water, Sucrose, Citric Acid

TABLE 4

Effect of taste compounds on the contribution of odour compounds to overall strawberry flavour using a n-0.5 omission protocol. The water sample is the control sample.

| COMPOUND | R INDEX (%) | | |
|---|---|---|---|
| | WATER | SUCROSE | CITRIC ACID |
| 2,3-Butanedione | 54.0 | 42.4 | 54.5 |
| Butanoic acid | 45.5 | 56.0 | 63.7* |
| Ethyl hexanoate | 47.1 | 51.8 | 55.3 |
| Methyl dihydrojasmonate | 49.8 | 40.5 | 59.3* |
| gamma-decalactone | 49.0 | 51.8 | 52.7 |
| 4-Hydroxy-2,5-dimethyl-3-furanone | 54.8 | 61.2* | 49.6 |
| Ethyl butanoate | 47.8 | 56.8 | 64.2* |
| cis-3-Hexen-1-ol | 53.8 | 53.5 | 46.6 |
| Methyl (E)-3-Phenylprop-2-enoate | 43.8 | 50.0 | 63.6* |

TABLE 5

Summary of the effect of taste compounds on the importance of odour compounds in the overall strawberry flavour.

| Level | WATER | R-INDEX (%) | WATER + SUCROSE | R-INDEX (%) | WATER + CITRIC ACID | R-INDEX (%) |
|---|---|---|---|---|---|---|
| LOW | Methyl (E)-3-Phenylprop-2-enoate | 43.8 | Methyl dihydrojasmonate | 40.5 | cis-3-Hexen-1-ol | 46.6 |
| | Butanoic acid | 45.5 | 2,3-Butanedione | 42.4 | 4-Hydroxy-2,5-dimethyl-3-furanone | 49.6 |
| | | | | | gamma-decalactone | 52.7 |
| MEDIUM | Ethyl hexanoate | 47.1 | Methyl (E)-3-Phenylprop-2-enoate | 50.0 | 2,3-Butanedione | 54.5 |
| | Ethyl butanoate | 47.8 | | | Ethyl hexanoate | 55.3 |
| | gamma-decalactone | 49.0 | gamma-decalactone | 51.8 | | |
| | Methyl dihydrojasmonate | 49.8 | Ethyl hexanoate | 51.8 | | |
| | | | cis-3-Hexen-1-ol | 53.5 | | |
| HIGH | cis-3-Hexen-1-ol | 53.8 | Butanoic acid | 56.0 | Methyl dihydrojasmonate | 59.3* |
| | 2,3-Butanedione | 54.0 | Ethyl butanoate | 56.8 | Methyl (E)-3-Phenylprop-2-enoate | 63.6* |
| | 4-Hydroxy-2,5-dimethyl-3-furanone | 54.8 | 4-Hydroxy-2,5-dimethyl-3-furanone | 61.2* | Butanoic acid | 63.7* |
| | | | | | Ethyl butanoate | 64.2* |

Surprising differences in the results with the different taste bases were observed. Of particular interest were the following:

n-Methyl (E)-3-phenylprop-2-enoate

This sample had an R-index of only 43.8% in the water study and although its value increased in the sucrose study to 50%, it still remained insignificant. It is interesting that it scored a perfect 50% which means the n−0.5 sample is perceived as identical to the original strawberry flavour (when in the presence of sucrose). However, in the presence of citric acid the results show its value increased dramatically and became significant at 63.6%. The results suggest that the presence of sucrose may compensate for the lack of methyl (E)-3-phenylprop-2-enoate but acid increases the effect of this compound on the overall strawberry flavour.

n-gamma-decalactone

There was very little difference in R-indices across all three trials for this sample. In the water sample it was 49%, in the sucrose 51.8% and in the citric acid 52.7%. Thus it appears that, in relation to this compound, it could be concluded that removing n-gamma-decalactone has little to no effect on the perception of the strawberry flavour, even in the presence of sucrose and citric acid.

n-4-Hydroxy-2,5-dimethyl-3-furanone

This sample comes out with the highest R-index for both the water and sucrose trials (54.8% and 61.2% respectively) but one of the lowest in the citric acid trial (49.6%) but it is only statistically significant in the sucrose trial. 4-Hydroxy-2,5-dimethyl-3-furanone is from the caramel block and it seems there is interaction with sucrose but no significant effect in water or in citric acid n-cis-3-Hexen-1-ol Insignificant in all three trials. It has a similar R-index for the water trial at 53.8% compared with the sucrose trial 53.5% but a much lower R-index for the citric acid trial at 46.6%. There is very little effect of sucrose on cis-3-Hexen-1-ol—unsurprising as it belongs to the green flavour block—this may change in the presence of other taste modalities.

n-Ethyl butanoate

The R-index for the water trial is 47.8% and 56.8% for the sucrose trial which are both statistically insignificant. However, it is one of the highest R-indices in the sucrose data set and in the citric acid data set it is the highest at 64.2% and statistically significant. Ethyl butanoate is part of the fruity/floral block so it would also be expected to be enhanced by the presence of citric acid as both occur naturally in strawberries and act congruently to provide the acidic/fruity profile of a strawberry's flavour. i.e in the citric acid trial, when it is removed and compared to the original strawberry sample (n), the citric acid enhances the effect of Ethyl butanoate in (n), making it easier to detect its absence in the Ethyl butanoate sample.

n-Ethyl hexanoate

Although none of the R-indices for this sample were significant, it was the only sample to be in the middle of its data set in all three trials. Against the other samples, this always performed the same within its set. From the fruity/floral flavour block it would have been expected to perform much higher in the tastant trials due to the properties of its aroma.

n-Methyl dihydrojasmonate

In the water and sucrose trials this sample had an insignificant effect but in the citric acid trial it reached an R-index of 59.3% to classify it as significant. It was the lowest R-index in the sucrose data set, at 40.5%, compared to the citric acid trial, This compound also has the greatest range between R-indices across the trials. From the fruity/floral block it would have been expected to perform high in the citric acid trial with congruency between acid and fruit.

n-2,3-Butanedione

All three trials had insignificant R-indices. In the water trial and the citric acid trial the R-index values were quite similar at 54.0% and 54.5% respectively. However, it was lower for the sucrose trial at only 42.4%.

2,3-Butanedione is from the buttery block so interactions with sugar and acid may not be expected.

n-Butanoic Acid

The citric acid trial is the only R-index which is statistically significant at 63.7%. The water trial was much lower at 45.5% and the sucrose trial was around the middle at 56%, with the citric acid and sucrose trials having R-indices in the highest range of each set.

Butanoic acid, from the buttery flavour block, and being an ionisable molecule is clearly affected greatly by the ionic state of the medium and its greater effect in citric acid may be due to the presence of more protonated molecules, which are volatile and therefore can contribute to aroma, compared to the ionised butanoic acid molecules.

Summary
- Tastants have significant effects on aroma compounds found to be insignificant in the retronasal trial—not previously appreciated or investigated.
- Although there is some congruency between fruity/floral flavours and citric acid, there are also a number of unexpected interactions which have not been previously reported and have only come to light as a result of applying the n−0.5 omission approach.
- Enhancement of caramel flavours by sucrose

Example 3

Sensory Methodology Comparison Test

The experiments were repeated as above but the compositions were formulated for smelling and tasting, with water, and were assessed using the n−1 methodology using the Same-Different test (ASTM-E2139-05) and Triangle test (ASTM-E1885-04). The Thurstonian distance d' is the degree of difference between the two samples tested. In this analysis, d' was used to assess the relative contribution of the different aroma compounds to the strawberry flavour and compare the performances of the Same-Different method with the Triangle method. For each omission test, d' was estimated using a ROC-fitting software (Hautus, M., SDT Assistant (Version 1.0) [Software]).

TABLE 6

Estimated d'values and variance ($S^2$) for samples delivered orthonasallyfor Same-Different method and Triangle Method.

| Omitted compound | Same-Different | | Triangle | |
|---|---|---|---|---|
| | d' | $S^2$ | d' | $S^2$ |
| 2,3-Butanedione | 1.10* | 0.06 | 0.80 | 0.19 |
| Butanoic acid | 1.39* | 0.05 | 0 | |
| Ethyl hexanoate | 1.38* | 0.05 | 1.24* | 0.11 |
| Methyl dihydrojasmonate | 1.52* | 0.03 | 0.09 | 11.3 |
| gamma-decalactone | 1.45* | 0.05 | 0.80 | 0.19 |
| 4-Hydroxy-2,5-dimethyl-3-furanone | 1.62* | 0.05 | 0.56 | 0.35 |
| Ethyl butanoate | 1.80* | 0.04 | 1.69* | 0.09 |
| cis-3-Hexen-1-ol | 1.82* | 0.04 | 0.69 | 0.24 |
| Methyl (E)-3-Phenylprop-2-enoate | 1.94* | 0.04 | 1.12* | 0.12 |

*Significant difference between omission sample and original sample (d' > 1)

Results in Table 6 shows that the Same-Different method gave higher d' values and was more discriminatory than the Triangle method when samples were delivered orthonasally. Carryover (particularly important for aroma samples), sensory fatigue and memory effects are more important in the triangle test, as more samples are assessed. However, when samples were delivered retronasally (Table 7), d' values obtained with the Same-Different method were not significantly higher compared to the Triangle method.

TABLE 7

Estimated d'values and variance ($S^2$) for samples delivered retronsally for Same-Different method and Triangle Method.

| Omitted compound | Same-Different | | Triangle | |
|---|---|---|---|---|
| | d' | $S^2$ | d' | $S^2$ |
| 2,3-Butanedione | 0.46 | 0.26 | 0 | |
| Butanoic acid | −0.59 | 0.18 | 0.39 | 0.67 |
| Ethyl hexanoate | −0.49 | 0.22 | 0.39 | 0.64 |
| Methyl dihydrojasmonate | −0.44 | 0.26 | 0.65 | 0.26 |
| gamma-decalactone | 0.18 | 1.45 | 0 | |
| 4-Hydroxy-2,5-dimethyl-3-furanone | 0.1 | 4.17 | 0.39 | 0.64 |
| Ethyl butanoate | −0.30 | 0.56 | 0.65 | 0.26 |
| cis-3-Hexen-1-ol | 0.65 | 0.13 | 0 | |
| Methyl (E)-3-Phenylprop-2-enoate | −0.55 | 0.18 | 0.9 | 0.16 |

*Significant difference between omission sample and original sample (d' > 1)

Summary
- The Same-Different method and associated Thurstonian distance d' constitutes an effective and robust sensory protocol for use in orthonasal omission experiments compared to Triangle testing method.
- Omission studies on orthonasal aroma do not necessarily represent perception retronasally.

Example 4

The aim of this Example was to apply the newly developed Same-Different approach to a savoury (i.e. not sweet) flavour.

Materials and Methods

Preparation of the Savoury Flavour

PG (by savoury it is meant, salty, meaty or spicy rather than sweet.

| Volatiles | Concentration in PG (mg/kg) | Top Level (g/100 g) | Prime Base (pb) (g/100 g) | Secondary Base (sb) (g/100 g) | Tertiary Base (tb) (g/100 g) |
|---|---|---|---|---|---|
| 2-furfurylthiol | 43.5 | 1 g sb | | 0.435 | |
| 4-Hydroxy-2,5-dimethyl-3-furanone | 13612.5 | 1.36 | | | |
| 3-mercapto-2-butanone | 103.5 | 1 g sb | | 1.035 | |
| 2-methyl-3-furanthiol | 36 | 1 g sb | | 0.36 | |
| Methional | 54 | 1 g sb | | 0.54 | |
| E,E-2,4-decadienal | 27 | 1 g sb | | 0.27 | |
| 12-methyltridecanal | 962 | 10 g pb | 0.96 | | |
| 1-octen-3-one | 9.4 | 10 g pb | 1 g tb | | 0.94 |
| Methylpropanal | 23.4 | 1 g sb | | 0.234 | |
| Indole | 70 | 1 g sb | | 0.7 | |

The savoury flavour stock was prepared as described in table 8 and Propylene glycol (PG) was used as a solvent. The savoury flavour stock was then diluted in Evian mineral water (DANONE Group, France) at 0.1% w/w.

Sensory Omission Study

Orthonasal delivery. Covered 20 mL glass bottles containing 10 mL of aroma sample were presented to the assessors. Assessors were instructed to sniff the samples and replace the lid immediately to prevent the aroma dispersing throughout the test area.

Sensory sessions. 100 naïve assessors were recruited among the students of the University of Nottingham. The session involved 10 discrimination tests. Assessors were instructed to assess the samples from left to right and were allowed to re-evaluate the samples if necessary. After every 2 tests, assessors were allocated a five minutes break to limit the sensory fatigue and carryover effects.

For each Same-Different test, the assessor had to assess the two samples and state whether they thought they were the same or different. Secondly, the assessors were asked to state the sureness level of their decision, represented by a four point surety scale (very unsure', 'unsure', 'sure', 'very sure'). A complete randomised balanced designed was used for the sample presentation. Fifty assessors were presented with a 'same pair' and the other fifty assessors were presented with a 'different pair'.

Estimation of d' for the Same-Different tests

Data were pooled from 100 assessors and a ROC fitting software (Hautus 2012) was used to model ROC curves based on maximum likelihood estimation and to estimate d' and its variance. As the likelihood-ratio (LR) model, associated with a beta-strategy, was shown to fit the data better than the differencing model; d' values were estimated using the LR model. The final estimate of d' was obtained by systematically adjusting the value to minimise the goodness of fit statistic chi-square corresponding to the normalised squared distance between each data points and the ROC curve.

Results

TABLE 9

Estimated d's and R-indices when 100% (n-1) or 50% (n-0.5) of the compound was removed from the model. Same-Different tests were used and samples were delivered orthonasally.

| Flavour block | Compound | n-1 R-index | n-1 d' (LR model) | n-0.5 R-index | n-0.5 d' (LR model) |
|---|---|---|---|---|---|
| meaty base | 2-furfurylthiol | 60.4* | 0.9877 | 59.6* | 0.9329 |
| | 4-Hydroxy-2,5-dimethyl-3-furanone | 60.42* | 0.9816 | 57.16 | 0.8595 |
| | 3-mercapto-2-butanone | 67* | 1.334† | 53.6 | 0.5874 |
| | 2-methyl-3-furanthiol | 62.2* | 1.106† | 46.58 | -0.412 |
| | Methional | 53.7 | 0.6139 | | |
| fatty base | E,E-2,4-decadienal | 44.2 | -0.6799 | | |
| | 12-methyltridecanal | 55.02 | 0.4645 | | |
| | 1-octen-3-one | 44.8 | -0.5036 | | |
| top note | Methylpropanal | 63.88* | 1.232† | 48.18 | -0.476 |
| | Indole | 56.7 | 0.732 | | |

Significant difference between omission sample and complete model:
†d' > 1or
*R-index > 59%

Results from omission experiment are presented in Table 9. The complete removal (n-1) of 4 out of 5 meaty compounds (2-furfurylthiol, 4-Hydroxy-2,5-dimethyl-3-furanone, 3-mercapto-2-butanone and 2-methyl-3-furanthiol) had a significant impact on the perception of the savoury flavour. The meaty compound, 2-furfurylthiol appears to be one of the main compounds of the flavour as its removal is still significant at n-0.5, The complete removal of Methylpropanal (n-1) also had a significant impact on the flavour.

In conclusion, the Same-Different approach can be applied to savoury flavour in the context of omission studies. It has significantly detected the removal of 5 out of 10 compounds from the flavour model, as well as the removal of 50% of 2-furfurylthiol.

Example 5

Experiments have also been carried out whereby the amount of one or more components were reduced by 25% i.e. n-0.25 of each compound(s) to be tested remained in the composition. These studies show that certain compounds (savoury or sweet) may also be detected at a level of 75% and perceived to affect the overall flavour of a composition.

The invention claimed is:

1. A method of analysing the components of a flavour sample comprising:
   a) preparing a first composition comprising a number (n) of aroma and/or taste compounds to form a replica of the flavour;

b) preparing a second composition comprising the same aroma and/or taste compounds as the first composition with only one of the aroma and/or taste compounds being reduced in amount by from 5 to 95% compared to the amount of the same aroma and/or taste compound in the first composition; and c) comparing the aroma and/or taste of the first and second compositions using only human sensory evaluation.

2. The method of claim 1, further comprising producing a further composition comprising the same aroma and/or taste compounds as the first composition, with a different one of the compounds than that changed in the second composition being reduced in amount by from 5 to 95% compared to the amount in the first composition; and wherein step c) comprises comparing the first, second and further compositions.

3. The method of claim 1, further comprising producing a further composition wherein the same compound is altered as in the second composition but to a different level; and wherein step c) comprises comparing the first, second and further compositions.

4. The method of claim 1, further comprising recording the results of the comparison of the first and second compositions, and carrying out statistical analysis of the results.

5. The method of claim 1, wherein the comparison of step c) is carried out by smell.

6. The method claim 1, wherein the comparison of step c) is carried out by taste.

7. The method of claim 1, wherein the first and second composition further comprise a sweet tasting compound.

8. The method of claim 1 wherein the first and second composition further comprise an acidic component.

9. The method according to claim 1, wherein the compound that is reduced in the second or further composition is reduced by 10 to 90%.

10. The method according to claim 1, wherein the compound that is reduced in the second or further composition is reduced by 20 to 80%.

11. The method according to claim 1, wherein the compound that is reduced in the second or further composition is reduced by 30 to 70%.

12. The method according to claim 1, wherein the compound that is reduced in the second or further composition is reduced by 40 to 60%.

13. The method according claim 1, wherein the compound that is reduced in the second or further composition is reduced by about 50%.

14. The method according to claim 1, wherein the compound that is reduced in the second or further composition is reduced by about 25%.

15. The method of claim 1, wherein the first and second composition further comprise a bitter tasting component.

16. The method of claim 1, wherein the first and second composition further comprise a salty tasting component.

17. The method of claim 1 wherein the first and second composition further comprise an umami tasting component.

18. The method of claim 1, wherein the human sensory evaluation comprises ASTM-E2139-05.

19. The method of claim 1, further comprising producing a further composition wherein the concentration of more than one compound is altered; and wherein step c) comprises comparing the first, second and further compositions.

* * * * *